US008859830B2

(12) United States Patent
Myers

(10) Patent No.: US 8,859,830 B2
(45) Date of Patent: Oct. 14, 2014

(54) METHODS AND ASSEMBLIES FOR LIQUID-PHASE REACTIONS

(75) Inventor: John D. Myers, Baton Rouge, LA (US)

(73) Assignee: Dow Global Technologies Inc., Midland, MI (US)

( * ) Notice: Subject to any disclaimer, the term of this patent is extended or adjusted under 35 U.S.C. 154(b) by 471 days.

(21) Appl. No.: 12/717,800

(22) Filed: Mar. 4, 2010

(65) Prior Publication Data

US 2011/0060173 A1    Mar. 10, 2011

Related U.S. Application Data

(60) Provisional application No. 61/157,645, filed on Mar. 5, 2009.

(51) Int. Cl.
| | | |
|---|---|---|
| *C07C 17/16* | (2006.01) | |
| *B01D 53/14* | (2006.01) | |
| *B01D 53/78* | (2006.01) | |
| *B01D 53/77* | (2006.01) | |

(52) U.S. Cl.
CPC ............... *B01D 53/78* (2013.01); *B01D 53/77* (2013.01); *B01D 53/1406* (2013.01); *B01D 2257/708* (2013.01); *C07C 17/16* (2013.01); *B01D 2257/80* (2013.01); *B01D 2257/2045* (2013.01)
USPC ...................................................... 570/258

(58) Field of Classification Search
CPC ..................................................... C07C 17/16
USPC ...................................................... 570/258
See application file for complete search history.

(56) References Cited

U.S. PATENT DOCUMENTS

| | | | |
|---|---|---|---|
| 2,847,484 A | 8/1958 | Kolker | |
| 3,502,733 A | 3/1970 | Kurtz et al. | |
| 3,981,938 A | 9/1976 | Steele et al. | |
| 3,983,180 A * | 9/1976 | Habata et al. ................. | 570/258 |
| 4,032,557 A | 6/1977 | Spork et al. | |
| 4,220,609 A | 9/1980 | McEntee et al. | |
| 4,271,132 A | 6/1981 | Eickmeyer | |
| 4,307,260 A | 12/1981 | Moore et al. | |
| 4,808,761 A | 2/1989 | Durand et al. | |
| 4,922,043 A | 5/1990 | Petrosky | |
| 4,935,564 A | 6/1990 | Bunce et al. | |
| 5,138,110 A | 8/1992 | Segall et al. | |
| 5,202,512 A | 4/1993 | Winkler et al. | |
| 5,917,099 A | 6/1999 | Narita et al. | |
| 6,111,153 A | 8/2000 | Crow et al. | |
| 2008/0287716 A1 | 11/2008 | Kaeppler et al. | |

FOREIGN PATENT DOCUMENTS

| | | |
|---|---|---|
| CN | 1323770 A | 11/2001 |
| CN | 1440958 A | 9/2003 |
| CN | 1515528 A | 7/2004 |
| CN | 1927789 A | 3/2007 |
| EP | 0059404 A1 | 9/1982 |
| EP | 0561554 A1 | 9/1993 |
| FR | 2270224 A1 | 12/1975 |
| IL | 86356 A | 5/1993 |
| JP | 52036604 A | 3/1977 |
| JP | 56150026 A | 11/1981 |
| JP | 57146727 A | 9/1982 |
| JP | 6001729 A | 1/1994 |
| JP | 6135864 A | 5/1994 |
| JP | 6135865 A | 5/1994 |
| JP | 6135866 A | 5/1994 |
| JP | 6172226 A | 6/1994 |
| JP | 2000063291 A | 2/2000 |
| JP | 2001288119 A | 10/2001 |
| RU | 2009117 C1 | 3/1994 |
| RU | 2041188 C1 | 8/1995 |
| RU | 2070188 C1 | 12/1996 |
| RU | 2079478 C1 | 5/1997 |
| RU | 2106335 C1 | 3/1998 |
| RU | 2127245 C1 | 3/1999 |
| RU | 2152920 C2 | 7/2000 |
| RU | 2242452 B | 12/2004 |
| RU | 2003125153 A | 12/2004 |
| WO | 2005026089 A2 | 3/2005 |

OTHER PUBLICATIONS

Dudukovic (Catalysis Today 48 (1999) 5-15).*
Vol'Kenshtein et al., "Initiation of the high-temperature reaction of tetrachloroethylene with methyl alcohol", Inst. Org. Khim. im. Selinskogo, 1972, pp. 2601-2603, (11), Moscow, USSR.
International Search Report and Written Opinion for International Application No. PCT/US2010/026255.

* cited by examiner

*Primary Examiner* — Robert Havlin
(74) *Attorney, Agent, or Firm* — Lois K. Ruszala; KSJLaw, LLC

(57) ABSTRACT

Methods and assemblies for improving the reaction kinetics of, conserving reactants utilized in, and/or producing a more pure reaction product of, liquid-phase reactions that involve volatile reactants and products are provided. The methods and assemblies herein provide for a feed of reaction liquid to two or more absorption zones, wherein the temperature and/or feed rate of the liquid is independently adjusted prior to introduction into at least one of the two or more absorption zones. More particularly, the temperature and feed rate of the liquid as delivered to each absorption zone can be adjusted independently to optimize the absorption of at least a portion of any gaseous reactants and byproducts from the gaseous product stream and/or to optimize reaction zone conditions. Reaction kinetics may thus be improved, or substantially maintained.

4 Claims, 1 Drawing Sheet

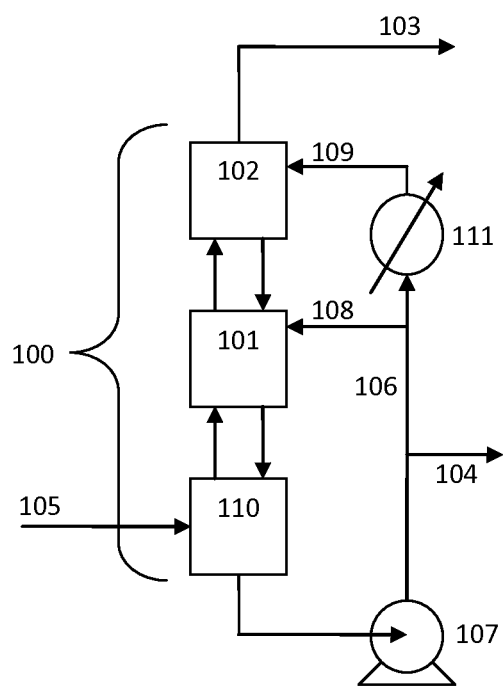

METHODS AND ASSEMBLIES FOR LIQUID-PHASE REACTIONS

FIELD

The present invention relates to methods and assemblies for liquid-phase reactions wherein gaseous reactants and byproducts are removed from the gaseous product and returned to the reaction. More specifically, the methods and assemblies disclosed herein can improve the reaction kinetics of liquid phase reactions and comprise a reaction zone and at least two absorption zones that utilize a liquid formed by, or utilized in, the liquid-phase reaction.

BACKGROUND

In liquid-phase reactions wherein gaseous products are produced, it is often desirable, if not necessary, to separate the gaseous product from any gaseous reactants remaining from, or byproducts produced by, the liquid-phase reaction. The recovery of said unreacted reactants and reaction byproducts from such reactions can pose many manufacturing difficulties, and in the least can be energy intensive. Performing such separations by cooling the reactor effluent and returning the condensed material to the reactor can undesirably reduce the operating temperature within the reactor, which can, in turn, hinder the reaction kinetics. Performing such separations by absorbing the reactor effluent into a cool liquid medium and returning the absorbed material to the reactor can have the same cooling effect, as well as dilution of the reactor contents if a liquid other than the liquid in the reactor is used for absorption. Adding heat to overcome said cooling effect can be costly. Removal of added liquid used for absorption, either from the reactor or from the absorbed reactants and byproducts prior to returning the latter to the reactor, can also be costly.

Much research has thus been devoted to increasing the efficiency, and thus, decreasing the operating cost, of these processes. Many have proposed the implementation of one or more separate steps, such as distillation or absorption, to achieve separation of the gaseous reactor effluent. However, such separation steps may be the most energy and cost-intensive operations in many manufacturing processes. And, each additional step adds capital cost. Some have proposed the use of absorption fluids other than the liquid from the reactor for carrying out separation of the gaseous reactor effluent. However, any additional liquids can accumulate in the process and cause the need for further separation steps to remove reactants and reaction byproducts from the added liquid so that it can be recycled or increased effluent to purge it from the system.

Efficient, more cost effective methods for the production of gaseous products from liquid-phase reactions, specifically the production of alkyl halides by the liquid-phase hydrochlorination of the corresponding alcohol, are thus needed. Desirably, such methods would produce the desired product with savings of equipment cost, time or energy.

BRIEF DESCRIPTION

Provided herein are methods and assemblies for improving the reaction kinetics of liquid-phase reactions that involve volatile reactants and products. The methods and assemblies herein provide for a feed of reaction liquid to two or more absorption zones, wherein the temperature and/or feed rate of the liquid is adjusted prior to introduction into at least one of the two or more absorption zones. More particularly, the temperature and feed rate of the liquid as delivered to each absorption zone can be adjusted independently to optimize the absorption of at least a portion of any gaseous reactants and byproducts from the gaseous product stream and/or to optimize reaction zone conditions. Reaction kinetics may thus be improved, or substantially maintained. In the latter embodiment, absorption performance may be improved such that reactants may advantageously be conserved, and a more pure gaseous product may be produced. The liquid may then be recycled to make use of the reactants absorbed therein. Further, the multiple-stage absorption process may be carried out in the same vessel as the reaction.

In one aspect, there is provided a method for improving the reaction kinetics of, conserving reactants utilized in, and/or producing a more pure reaction product of, of a liquid-phase reaction. In some embodiments, the reaction is the liquid-phase hydrochlorination of methanol to product methyl chloride. The method comprises providing at least a first and a second absorption zone and splitting a liquid from the reaction into at least a first stream and a second stream. The temperature and/or feed rate of at least one of the streams is adjusted and the first liquid stream is directed to the first absorption zone, and the second liquid stream is directed to the second absorption zone, where the streams come into contact with at least a portion of the gaseous product stream. Gaseous reactants and reaction byproducts are thus removed from the gaseous product stream and are absorbed into the liquid. By adjusting the temperature and/or feed rate of the liquid fed to one absorption zone and using said liquid at substantially the temperature and/or flow rate at which it exits from the reaction zone in another absorption zone, favorable reaction conditions within the vessel may be substantially maintained, and reaction kinetics improved or substantially maintained.

The method may advantageously be carried out in a single vessel, thereby avoiding the cost, time and space expenditure associated with additional separation equipment. And so, in a second aspect, an assembly for a liquid-phase reaction for the production of a gaseous product is provided. The assembly comprises a liquid reaction zone and at least two absorption zones. One or more conduits are provided to conduct liquid from the reaction zone to each of the absorption zones. At least one of the conduits has a temperature adjusting mechanism and/or flow rate adjusting mechanism operatively disposed relative thereto.

In certain embodiments, it may be desirable to further reduce the concentration of gaseous reactants and byproducts in the product stream or to otherwise further process the product stream. It may also be desirable to further process the liquid stream leaving the reactor to recover valuable reactants and return them to the reactor, or to subject the reactants to pre-processing prior to application of the present method, or introduction into the present reactor. As such, the assembly may comprise further processing equipment. The further equipment may comprise a preliminary reactor, such as another liquid-phase reactor or a gas phase reactor; or separation equipment, e.g., one or more strippers, scrubbers, distillation columns, reactors or combinations of these.

DRAWINGS

These and other features, aspects, and advantages of the present invention will become better understood when the following detailed description is read with reference to the accompanying drawings in which like characters represent like parts throughout the drawings.

FIG. 1 is a schematic illustration of a reactor in accordance with one aspect of the present invention.

DETAILED DESCRIPTION

Unless defined otherwise, technical and scientific terms used herein have the same meaning as is commonly understood by one of skill in the art to which this invention belongs. The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced item, and the terms "front", "back", "bottom", and/or "top", unless otherwise noted, are merely used for convenience of description, and are not limited to any one position or spatial orientation. If ranges are disclosed, the endpoints of all ranges directed to the same component or property are inclusive and independently combinable (e.g., ranges of "up to about 25 wt. %, or, more specifically, about 5 wt. % to about 20 wt. %," is inclusive of the endpoints and all intermediate values of the ranges of "about 5 wt. % to about 25 wt. %," etc.). The modifier "about" used in connection with a quantity is inclusive of the stated value and has the meaning dictated by the context (e.g., includes the degree of error associated with measurement of the particular quantity).

The suffix "(s)" as used herein is intended to include both the singular and the plural of the term that it modifies, thereby including one or more of that term (e.g., "the liquid stream(s)" may include one or more liquid streams). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described inventive features may be combined in any suitable manner in the various embodiments.

The term 'reaction zone', as used herein, is meant to indicate a space within which the majority of the desired reaction may typically occur. It is to be understood that the desired reaction, and others, may also take place in other spaces, including either or both absorption zones.

The methods and assemblies provided herein are described as being capable of improving, or substantially maintaining, the reaction kinetics of the liquid phase reactions to which they are applied, or that are carried out there. Improved reaction kinetics can allow for a reduction in the size and cost of the reactor assembly for any specified rate of production, or can increase the production rate of a given reactor. The improved reaction kinetics provided by the improved methods and assemblies described herein can also reduce the cost of or entirely eliminate conventional means for improving kinetics, which can use a greater amount of energy, require greater manufacturing space or require additional equipment, such as heat exchangers, heat exchanging solvents, etc. Reaction kinetics may also be substantially maintained, in which case, application of the principles described herein may advantageously provide for the use of lesser amounts of reactants, or the production of a more pure reaction product.

Provided herein are improved methods and assemblies for improving, or at least substantially maintaining, the reaction kinetics of liquid phase reactions. More specifically, the methods and assemblies provide for removing at least a portion of any gaseous reactants and reaction byproducts from the gaseous product stream of a liquid-phase reaction. Such separations, when carried out via conventional methods or with conventional assemblies, may detrimentally affect the reaction conditions, may be expensive, and disposal rather than reuse of recovered reactants can undesirably add to the overall cost of the process.

The inventive method and assembly comprise two or more feeds of reaction liquid to two or more absorption zones, wherein the temperature and/or feed rate of the liquid is adjusted prior to introduction into at least one of the two or more absorption zones. The temperature and feed rate of the liquid can be independently adjusted to optimize the absorption of at least a portion of any gaseous reactants and byproducts from the gaseous product stream in one zone, and in another zone, adjusted to optimize the reaction zone conditions. Reaction kinetics may thus be improved, or substantially maintained, and increased production realized in any given reactor size. In the latter embodiment, absorption performance may be improved such that reactants may advantageously be conserved, and a more pure gaseous product may be produced.

As those of ordinary skill in the art are aware, gases may typically be more soluble in cooled liquids. Many conventional methods and assemblies for the removal of gaseous reactants or byproducts from a gaseous product stream may utilize recycled reaction liquid streams, and any such recycled reaction liquid streams are typically cooled in efforts to remove as much of the gaseous reactants and/or reaction byproducts from the gaseous product stream as possible. However, the extensive cooling of the recycled reaction liquid required to allow the liquid to absorb the desired maximum amount of reactants and by products from the product stream, coupled with the conventional use of only one absorption zone, results in an undesirable reduction in temperature of the reaction environment when the liquids are returned to the reactor. Reaction kinetics in such conventional methods and assemblies thus suffers.

In contrast, the present methods make use of a liquid generated by, or utilized in, the liquid-phase reaction to absorb gaseous reactants or byproducts in at least two absorption zones. In one zone, a recycled liquid may be utilized at substantially the same temperature at which it was produced or utilized within the reaction zone, the reaction temperature, or only slightly cooled, and at substantially the same feed rate at which it exits the reaction zone. In another zone, the recycled reaction liquid may be chilled to a greater degree than the first zone, or delivered at a different feed rate than the first zone, to increase the solubility of any gaseous reactants or reaction byproducts therein. In this way, significant cooling of the reaction zone may be minimized. And, the purity of the gaseous product, the yield of the process, and/or the cost efficiency of the process, may be enhanced.

It is to be understood that in some processes, the liquid may desirably be heated for use in one or more absorption zones, chilled in one or more absorption zones, or utilized at substantially the reaction temperature in one or more absorption zones. Also, the liquid may be delivered at the same rate at which it exits the reaction zone, or at a slower or faster rate. The inventive concept of the methods and assemblies disclosed herein are not limited to particular embodiments or combinations, but rather extend to any method or assembly for liquid phase reactions wherein improved reaction kinetics would be desirable, and in particular, to any such reaction wherein gaseous reactants or byproducts are desirably removed from a gaseous product stream and recycled. All that is required is that the method and/or assembly utilizes or provides at least two absorption zones, wherein in one absorption zone the temperature and/or feed rate of the liquid is/are optimized for removal of any gaseous reactants or reaction byproducts therein, and in another zone, the temperature and/or feed rate of the liquid is optimized to substantially maintain reaction conditions within the reaction zone.

The particular conditions, e.g., temperature, pressure etc., of each absorption zone will depend upon the particular gaseous reactants and byproducts desirably removed from the gaseous product stream and the solubility of the reactants and/or reaction byproducts in the liquid. Based upon this information, those of ordinary skill in the art would be capable of implementing appropriate conditions for each stage, i.e., that in one instance would optimize the solubility of the reactants/reaction byproducts therein, and in another, would provide more limited but yet significant solubility without adversely affecting the desired operating conditions within the reaction zone.

For exemplary purposes only then, in one absorption zone the liquid may be utilized at substantially the temperature and/or feed rate at which it is utilized or generated within the reactor to affect the bulk absorption of gaseous reactants and byproducts while yet maintaining the desired reaction conditions within the reaction zone. For the exemplary reaction of the liquid phase hydrochlorination of methanol, the temperature of the liquid as utilized or generated may be, e.g., from about 50° C. to about 200° C., or may be only slightly cooled, e.g., from about 0° C. to 50° C. below the temperature at which it is utilized or generated. In another absorption zone, the liquid may be chilled to a lower temperature of from just above freezing to about 5° C. below the temperature of the reaction zone, or delivered at a different feed rate, or both, to enhance the solubility of reactants and reaction byproducts therein.

Although the exemplary temperature ranges for the two absorption zones overlap, the cooling of liquid fed to one absorption zone may generally be to a lower temperature than the cooling, if any, of the other absorption zone. In this manner, the zone with the lower temperature and/or faster feed rate will provide enhanced solubility of the gaseous reactants and byproducts desirably absorbed. The temperature and/or feed rate of the other zone will also allow for significant solubility of gaseous reactants and by products desirably absorbed, while also assisting in maintaining the desired reaction conditions within the reaction zone. Desirably, the zone capable of assisting in maintaining the desired conditions within the reaction zone will be operatively disposed proximal thereto, while the absorption zone with the lower temperature and/or faster feed rate will be operatively disposed distal to the reaction zone.

One example of a reaction that may benefit from the principles described herein is hydrochlorination of alkanols to produce the corresponding alkyl halide, and particularly alkyl halides comprising from one to four carbon atoms. Such liquid-phase hydrochlorination reactions may be carried out with gaseous or liquid reactant feeds, and in the presence of, or without, catalysts. The principles described herein may be applied to any of these, or to combinations of any of these.

In such reactions, the gaseous product stream will comprise not only the desired product, i.e., the alkyl halide, but also the alkanol, water vapor, and hydrogen halide, while the reaction liquid will comprise essentially the same components, except that the hydrogen halide will be predominantly in a dissociated state within the reaction liquid.

Although some conventional alkanol hydrochlorination processes may utilize a recycled reaction liquid feed to absorb gaseous reactants and byproducts from the gaseous product stream, in order to maximize the solubility of the reactants and reaction byproducts therein, any such recycled reaction liquid is typically chilled, e.g., to a temperature significantly below the reaction temperature but above its freezing point. As a result, and because of the large volume of chilled liquid required to adequately absorb the desired amount of the gaseous reactants and byproducts, reintroduction of the chilled reaction liquid into the reaction zone typically results in the significant cooling thereof. Reaction kinetics are thus hindered.

In contrast, when the principles disclosed herein are applied to hydrochlorination reactions and at least two absorption zones are utilized, the reaction liquid may be utilized in a first absorption zone, proximal to the reaction zone, at substantially the reaction temperature, e.g., from about 50° C. to about 200° C., and at substantially the same flow rate as it exits the reaction zone, to perform part of the required absorption without adversely affecting the reaction conditions within the reaction zone. In a second absorption zone, the liquid may be utilized at a temperature significantly below the reaction temperature, e.g., from just above the freezing point to about 150° C., and/or be delivered at an altered feed rate relative to the rate at which it exits the reactor to facilitate further absorption of methanol, hydrogen chloride and/or water vapor therein.

In such embodiments, and in the case with any liquid-phase reaction as described above, the absorption zones/processes may be arranged or carried out serially or may be arranged or carried out in parallel. Desirably, the multiple absorption zones are arranged, or the absorptions carried out, serially with respect to gas flow.

In a first absorption zone, the liquid is utilized substantially at the temperature and/or feed rate at which it is generated, i.e., little or no external heating or cooling means is applied. If cooling is applied, or the feed rate is altered, it is less that the level of cooling, or the feed rate altered to a lesser extent than that applied to the subsequent absorption zone in a multi-zone system. As a result, bulk absorption of hydrogen chloride and methanol can take place, while yet the reaction zone temperature is not significantly cooled.

In a second absorption zone, the reaction liquid may desirably be cooled, e.g., to from about 1° C. below the reaction temperature to just above the freezing point of the liquid, and/or the flow rate of the liquid may be altered. Since bulk absorption of methanol and hydrogen chloride has already been carried out in a first absorption zone, a slower feed rate or overall smaller volume of cooled reaction liquid is expected to be required to achieve the desired reduction of reactants and reaction byproducts in the gaseous product. Compared to a system with only a single zone of absorption, overall cooling of the reaction zone may be reduced, while yet providing methyl chloride with the desired purity and at the desired yield. Furthermore, the necessity of application of further separation or drying techniques to the gaseous product stream may be reduced or eliminated.

The methods disclosed herein can thus provide significant cost savings, increased efficiency and reuse of reactants and reduction or elimination of the use of further separation or drying steps. In some embodiments, these cost savings can be further leveraged by providing one or both of the absorption zones within a single reaction vessel. In this manner, the energy expense required to power additional equipment, and the manufacturing footprint required by the same, can be reduced. And so, the present disclosure also provides an assembly for a liquid-phase reaction that produces a gaseous product stream.

Typically, such assemblies comprise multiple feeds for the reactants, as well as any products or byproducts from upstream reactors or feed processing operations. These may include any of the reactants or products mentioned thus far, as well as dialkylether and alkane, which can be byproducts of the desired reaction in the case of the exemplary liquid phase hydrochlorination reaction of methanol. The feeds might also include carriers such as water required for the reaction to initiate or continue.

Desirably, there are at least provided feeds for the reactants, which in hydrochlorination reactions may comprise, e.g., methanol, which can be introduced as a liquid or gas, and hydrogen chloride, which can be introduced as a gas or aqueous solution. Any of the feeds to the system may be arranged in any configuration and enter at any location on the reactor or absorption stages.

The reaction zone may comprise any type of reactor appropriate for conducting the desired liquid-phase reaction. Such reactors may typically include packed columns or boiling beds operated either adiabatically or heated and either as a plug flow or perfectly mixed device, or any configuration in between. In those embodiments wherein the reaction zone and assembly are desirably utilized for the production of, e.g., methyl chloride, the reactor may desirably comprise a countercurrent absorption column with or without a liquid reservoir at the bottom to provide higher liquid residence time, with the feeds of methanol and hydrogen chloride being appropriately configured to provide such countercurrent flow. The absorption equipment associated with gaseous feed introduction into the reactor can be the same as that utilized in the absorption zones or, separate zones may be provided specifically for feed absorption.

The liquid-phase reaction occurs in the liquid phase, and liquid generated by, or utilized in, the reaction may typically collect in the bottom of the reactor. At least one conduit may be provided to connect the reaction zone and/or bottom of the reactor with each of the absorption zones. The at least one conduit may be split to provide individual feeds to the absorption zones, or separate conduits may be provided for each absorption zone. Desirably, a temperature adjusting mechanism and/or feed rate adjusting mechanism is operatively disposed relative to at least one of the conduits, so that the temperature and/or feed rate of the liquid therein may be adjusted so that the ability to absorb reactants and/or reaction byproducts therein is optimized, or so that the adjusted temperature and/or feed rate of the liquid assists in the maintenance of the desired reaction conditions within the reaction zone.

One embodiment of an assembly 100 in accordance with the present invention is shown in FIG. 1. As shown, assembly 100 may comprise a reaction zone 110, first absorption zone 101, second absorption zone 102, gaseous product line 103, liquid byproduct line 104, feed 105, liquid conduit 106, pump 107, first absorption zone conduit 108, second absorption zone conduit 109 and chiller 111. Although operation of assembly is described with specific reference to the hydrochlorination of methanol, it is to be understood that the invention is not so limited, but rather, the assembly and method may be utilized in connection with any liquid phase reaction that produces a gaseous product stream.

In operation, the desired feeds, e.g., hydrogen chloride, methanol, and possibly a product stream from a previous reactor or process, enter reaction zone 110, with an inlet temperature of 0 to 500° C., and reaction zone conditions comprising a temperature of from about 80° C. to 200° C. and a pressure of from about 20 psig to about 200 psig. The liquid-phase reaction takes place in reaction zone 110 and, to a lesser extent, in the liquid-phase of absorption zones 101 and 102. The liquid generated by, or utilized in the reaction, comprising, e.g., water, hydrogen chloride, methanol, methyl chloride and dimethyl ether, is collected at the bottom of reaction zone 110. Conduit 106, powered by pump 107, circulates liquid from reaction zone 110 to first absorption zone 101 and second absorption zone 102.

More particularly, in the embodiment shown, first absorption zone conduit 108 provides reaction liquid to first absorption zone 101 without substantially altering the conditions thereof. First absorption zone 101 may comprise any equipment capable of facilitating the absorption of at least a portion of any gaseous reactants and/or byproducts into the liquid. Once the liquid passes through first absorption zone 101, it recollects in reaction zone 110.

Second absorption zone conduit 109 provides liquid from the bottom of reaction zone 110 to second absorption zone 102 via liquid recirculation conduit 106, assisted by pump 107. More particularly, liquid circulation conduit 106 bifurcates into first absorption zone conduit 108 and second absorption zone conduit 109. Second absorption zone conduit 109 is provided with chiller 111 operatively disposed relative thereto. Chiller 111 reduces the temperature of the liquid within second absorption zone conduit 109 to from about the reaction liquid freezing point to about 5° C. below the temperature of the liquid in reaction zone 110, thereby facilitating the absorption of reactants or reaction byproducts therein. It is to be understood that chiller 111 may be replaced by, or second absorption zone conduit 109 may further comprise in addition to chiller 111, a second pump (not shown) in addition to pump 107. Methyl chloride, comprising from about 0 to about 5 weight % methanol, from about 0 to about 5 weight % HCl, and from about 0 to about 5 weight % water vapor is released from gaseous product line 103.

Liquid, having absorbed therein methanol, HCl, etc. passes through second absorption zone 102 and into first absorption zone 101 where it may be combined with liquid provided to first absorption zone 101 and further utilized for absorption. The amount of cooled liquid required to affect the desired amount of absorption in second absorption zone 102 is minimized by the bulk absorption accomplished in first absorption zone 101. Thus, desirably, reaction zone 110 will be maintained substantially at the desired reaction conditions, e.g., for hydrochlorination reactions, a temperature of from about 50° C. to about 200° C. depending on the pressure of operation.

Although some embodiments of the reactor disclosed herein may reduce or eliminate the need or desire for the utilization of further processing equipment to separate or dry the gaseous reaction product, to pre-process the reactants, or to recover reactants from the liquid byproduct from reaction zone 110, in some environments, the use of such additional equipment may be desired or required. So, in further embodiments, the assembly may comprise further processing equipment.

The further processing equipment provided will depend on the liquid-phase reaction being carried out, and the intended application of the gaseous product produced thereby, and so, may include any piece of processing equipment that may further purify or dry the gaseous reaction product, or provide the reaction product in the desired configuration for its intended use. Or, the further processing equipment may include equipment to preprocess any of the reactants, or even may comprise an additional liquid-phase or gas-phase reactor, so that the product stream produced thereby is provided into the assembly disclosed herein. The further processing equipment may also include equipment to strip and recycle valuable reactants from the liquid byproduct stream e.g., water, formed in the reaction.

While not exhaustive, the examples below are provided to further illustrate some of the principles of the present invention.

Example 1

Comparative

An reactor assembly was prepared comprising a reaction zone, and a single absorption zone. The absorption zone was a packed section through which the gaseous product stream was scrubbed to remove water, methanol and HCl. The absorption zone was plumbed to receive liquid from the reaction zone through a conduit provided with a chiller, so that the liquid had a temperature of about 35° C.

The feed to the reactor assembly was a gas from a catalytic reactor containing HCl, methyl chloride and water (with small amounts of dimethylether and unreacted methanol) and was fed to the vapor space between the reaction zone and absorption zone. The amount of excess HCl fed to the catalytic reactor was varied to maintain 18-22% HCl concentration in the liquid contained in the bottom of the reaction zone. Liquid methanol was additionally fed to the reactor assembly. The ratio of methanol fed to the reactor assembly to the volume of the liquid in the bottom of the reaction zone was 560 Kg/Hr/m$^3$. Cooled liquid from the reaction zone was fed to the absorption zone at a rate of 169 gpm to maintain the temperature of the gas leaving the absorption zone below 45° C. At these conditions, the reaction zone had a temperature of 106° C. and a methanol concentration 10% by weight.

Example 2

The conditions of Example 1 were repeated, except that the provided assembly comprised a reaction zone, and two absorption zones. The first absorption zone was provided below the second absorption zone and comprised a packed section to scrub water, methanol and HCl from the gaseous product stream, and plumbed to receive liquid from the reaction zone. 220 gpm of liquid was fed from the reaction zone to the packing of the first absorption zone. This liquid was cooled only minimally by about 14° C.

The second absorption zone was a packed section through which the gaseous product stream was further scrubbed to remove water, methanol and HCl. The second absorption zone was plumbed to receive liquid from the reaction zone through a conduit provided with a chiller, so that the liquid provided to the second absorption zone had a temperature of about 35° C. At these conditions, the required amount of cooled liquid feed to the second absorption zone to maintain the gas temperature leaving the second absorption zone below 45° C. was 90 gpm. The liquid in the reaction zone had a temperature of 115° C. and methanol concentration 5% by weight.

As illustrated by these examples, the use of the method and assembly described herein resulted in the temperature within the reaction zone being maintained 9° C. higher than the example using only a single-stage chilled absorption. The more favorable reaction kinetics afforded by the higher temperature resulted in reduced methanol (i.e., reactant) concentration from about 10% to 5% in the reaction liquid.

While various embodiments of the present invention have been shown and described herein, it will be understood that such embodiments are provided by way of example only and not of limitation. Numerous variations, changes and substitutions will occur to those skilled in the art without departing from the teaching of the present invention. Accordingly, it is intended that the invention be interpreted within the full spirit and scope of the appended claims.

The invention claimed is:

1. A method for the hydrochlorination of one or more alkanols to produce a gaseous product stream of one or more alkyl halides, the method comprising:
   Providing a vessel comprising a reaction zone and at least a first absorption zone proximal to the reaction zone and a second absorption zone distal to the reaction zone;
   Splitting a portion of a liquid from the reaction zone into at least a first liquid stream and a second liquid stream and adjusting the temperature of at least one of the liquid streams so that the temperature of the first stream is higher than the temperature of the second stream;
   Directing the first liquid stream to the first absorption zone, and the second liquid stream to the second absorption zone; and
   Causing at least a portion of the gaseous product stream leaving the reaction zone and at least a portion of the first liquid stream to come into contact within the first absorption zone and at least a portion of the gaseous product stream leaving the first absorption zone and at least a portion of the second liquid stream to come into contact within the second absorption zone;
wherein the splitting consists of splitting the liquid via a bifurcated conduit or multiple conduits operably disposed relative to the reaction zone and wherein at least a portion of any gaseous reactants or gaseous by-products within the gaseous product stream are absorbed into the first and second liquid streams from the reaction zone.

2. The method of claim 1, wherein the method further allows for a desired reaction temperature within the reaction zone to be substantially maintained.

3. The method of claim 1, further comprising returning at least a portion of the liquid leaving the first and/or second absorption zone and having at least a portion of the gaseous reactants or gaseous by-products absorbed therein to the reaction zone.

4. The method of claim 1, further comprising additional steps to remove at least a portion of any gaseous reactants or by-products remaining in the gaseous product stream.

\* \* \* \* \*